(12) United States Patent
Prangenberg

(10) Patent No.: US 11,303,824 B2
(45) Date of Patent: Apr. 12, 2022

(54) VEHICLE-MOUNTED REMOTE SURVEILLANCE PTZ VIDEO CAMERA ASSEMBLY COMPRISING A PAIR OF ARTICULATED ARMS EACH COUPLED WITH A RESPECTIVE CAMERA

(71) Applicant: John Prangenberg, Camarillo, CA (US)

(72) Inventor: John Prangenberg, Camarillo, CA (US)

( * ) Notice: Subject to any disclaimer, the term of this patent is extended or adjusted under 35 U.S.C. 154(b) by 0 days.

(21) Appl. No.: 16/996,333

(22) Filed: Aug. 18, 2020

(65) Prior Publication Data

US 2022/0060637 A1   Feb. 24, 2022

(51) Int. Cl.
| | |
|---|---|
| *H04N 5/247* | (2006.01) |
| *B60R 11/04* | (2006.01) |
| *H04N 5/232* | (2006.01) |
| *H04N 7/18* | (2006.01) |
| *H04N 5/225* | (2006.01) |

(Continued)

(52) U.S. Cl.
CPC ............ *H04N 5/247* (2013.01); *B60R 11/04* (2013.01); *F16M 11/02* (2013.01); *G08B 13/19617* (2013.01); *H04N 5/2251* (2013.01); *H04N 5/2252* (2013.01); *H04N 5/2253* (2013.01); *H04N 5/2257* (2013.01); *H04N 5/2258* (2013.01); *H04N 5/23206* (2013.01); *H04N 5/23296* (2013.01); *H04N 5/23299* (2018.08); *H04N 7/181* (2013.01); *H04W 4/38* (2018.02); *A61B 6/4458* (2013.01); *B25J 9/046* (2013.01); *B25J 17/0283* (2013.01); *B25J 19/02* (2013.01); *B25J 19/023* (2013.01); *B60R 2300/00* (2013.01); *F16M 2200/06* (2013.01)

(58) Field of Classification Search
CPC .... H04N 5/247; H04N 7/181; H04N 5/23206; H04N 5/23296; H04N 5/23299; H04N 5/2251; H04N 5/2252; H04N 5/2253; H04N 5/2254; H04N 5/2257; H04N 5/2258; G08B 13/19617–19663; H04W 4/38; B60R 11/04; B60R 11/00; B60R 2300/00; B25J 19/023; B25J 19/02; B25J 9/046; B25J 17/0283; A61B 6/4405; A61B 6/4458; F16M 2200/06–068
USPC ................ 348/36–39, 42, 47, 148–149, 159, 348/211.1–211.14, 211.99, 373–376
See application file for complete search history.

(56) References Cited

U.S. PATENT DOCUMENTS

| | | |
|---|---|---|
| 6,583,730 B2 | 6/2003 | Lang |
| 9,083,868 B2 * | 7/2015 | Galindo Verdasco ...................... F16M 13/027 |

(Continued)

*Primary Examiner* — James M Hannett
*Assistant Examiner* — Akshay Trehan

(57) ABSTRACT

A remote surveillance assembly includes a base that is positionable in a vehicle and a pole that is coupled to and extends upwardly from the base. A pan tilt zoom (PTZ) video camera is movably disposed on the pole to capture surveillance of the environment around the vehicle. A pair of articulated arms is each of the articulated arms is movably coupled to the pole. A pair of digital cameras is each coupled to a respective one of the articulated arms to capture surveillance of the environment around the vehicle. A digital video recorder is coupled to the base and a transceiver is coupled to the base. The transceiver is in wireless communication with an extrinsic communication network to broadcast the data stored in the digital video recorder to a remote data storage device.

14 Claims, 6 Drawing Sheets

(51) Int. Cl.
*G08B 13/196* (2006.01)
*F16M 11/02* (2006.01)
*H04W 4/38* (2018.01)
*B25J 9/04* (2006.01)
*B25J 17/02* (2006.01)
*B25J 19/02* (2006.01)
*A61B 6/00* (2006.01)

(56) References Cited

U.S. PATENT DOCUMENTS

| | | | |
|---|---|---|---|
| 10,011,230 B1* | 7/2018 | Brown | G06V 10/147 |
| 2002/0167587 A1 | 11/2002 | Ogasawara | |
| 2005/0206741 A1 | 9/2005 | Raber | |
| 2006/0028548 A1* | 2/2006 | Salivar | H04N 7/181 |
| | | | 348/143 |
| 2006/0119701 A1* | 6/2006 | King | A61B 90/361 |
| | | | 348/E7.086 |
| 2007/0291123 A1 | 12/2007 | Cole | |
| 2010/0201813 A1 | 8/2010 | Monsive | |
| 2010/0225738 A1* | 9/2010 | Webster | B60R 11/04 |
| | | | 348/36 |
| 2010/0271497 A1* | 10/2010 | Monsive, Jr. | H04N 7/185 |
| | | | 348/211.99 |
| 2014/0111683 A1* | 4/2014 | Galindo Verdasco | |
| | | | F16M 11/10 |
| | | | 348/373 |
| 2016/0358435 A1* | 12/2016 | Lee | H04N 7/183 |
| 2017/0171436 A1* | 6/2017 | Fagerkvist | F16C 11/04 |
| 2017/0225321 A1* | 8/2017 | Deyle | B25J 9/1679 |
| 2018/0169873 A1* | 6/2018 | Gobin | B26D 5/007 |
| 2020/0288064 A1* | 9/2020 | Hirose | H04N 5/23299 |
| 2020/0374470 A1* | 11/2020 | Lyu | B25J 9/12 |

* cited by examiner

VEHICLE-MOUNTED REMOTE SURVEILLANCE PTZ VIDEO CAMERA ASSEMBLY COMPRISING A PAIR OF ARTICULATED ARMS EACH COUPLED WITH A RESPECTIVE CAMERA

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to surveillance device and more particularly pertains to a new surveillance device for remotely conducting covert surveillance.

(2) Description of Related Art Including Information Disclosed Under 37 CFR 1.97 and 1.98

The prior art relates to surveillance devices including a surveillance camera that is integrated into a rear view mirror of a vehicle. The prior art discloses a video camera that is recessed into a roof of a vehicle and which can be deployed outwardly from the roof. The prior art also discloses a variety of remote surveillance devices to facilitate a designated area to be remotely monitored with video surveillance. The prior art discloses a law enforcement vehicle camera system that is in wireless communication with a base station. The prior art also discloses a remote surveillance system for remotely conducting video and audio surveillance of an area.

BRIEF SUMMARY OF THE INVENTION

An embodiment of the disclosure meets the needs presented above by generally comprising a base that is positionable in a vehicle and a pole that is coupled to and extends upwardly from the base. A pan tilt zoom (PTZ) video camera is movably disposed on the pole to capture surveillance of the environment around the vehicle. A pair of articulated arms is each of the articulated arms is movably coupled to the pole. A pair of digital cameras is each coupled to a respective one of the articulated arms to capture surveillance of the environment around the vehicle. A digital video recorder is coupled to the base and a transceiver is coupled to the base. The transceiver is in wireless communication with an extrinsic communication network to broadcast the data stored in the digital video recorder to a remote data storage device.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
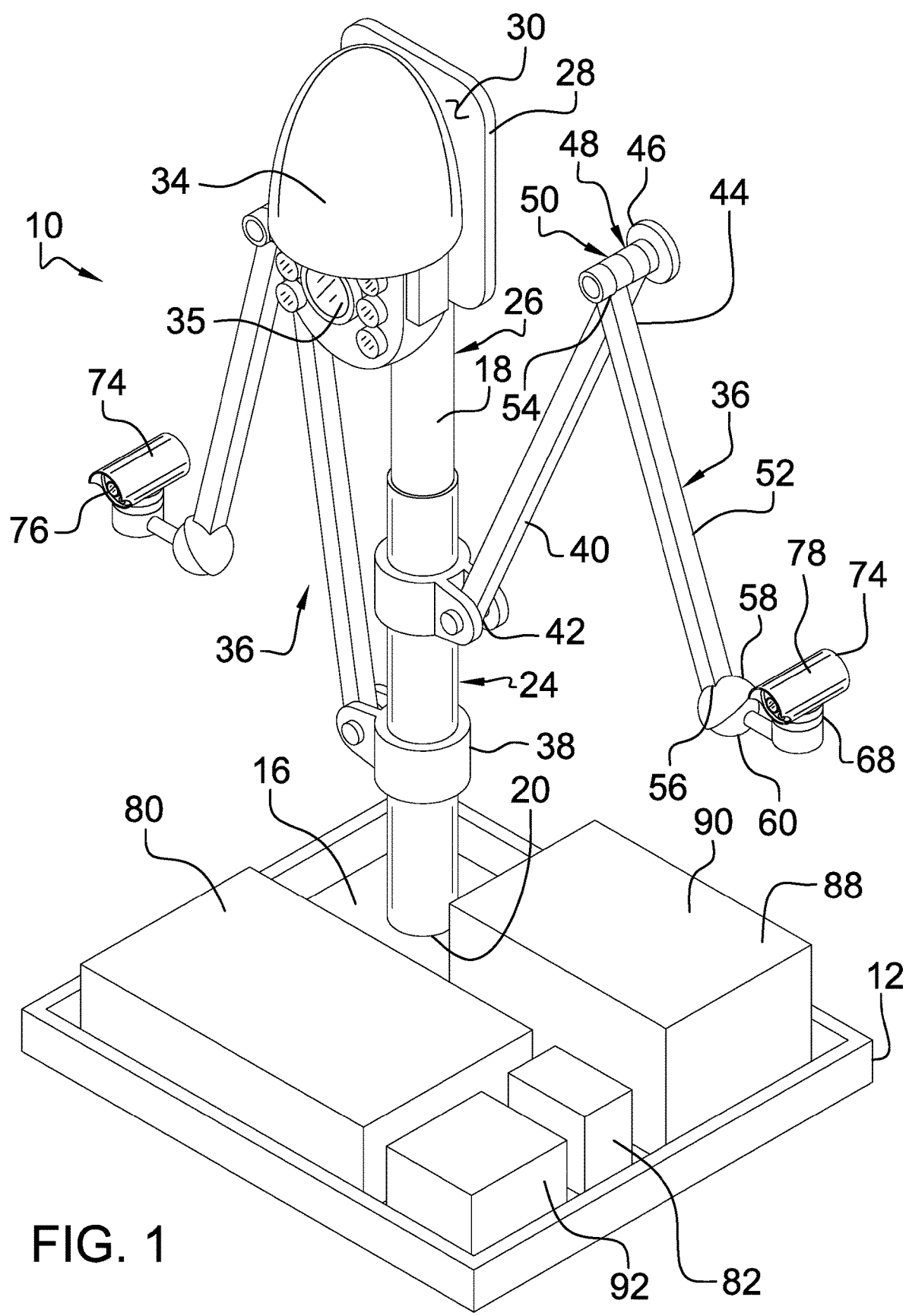
FIG. 1 is a front perspective view of a remote surveillance assembly according to an embodiment of the disclosure.
Figure 2:
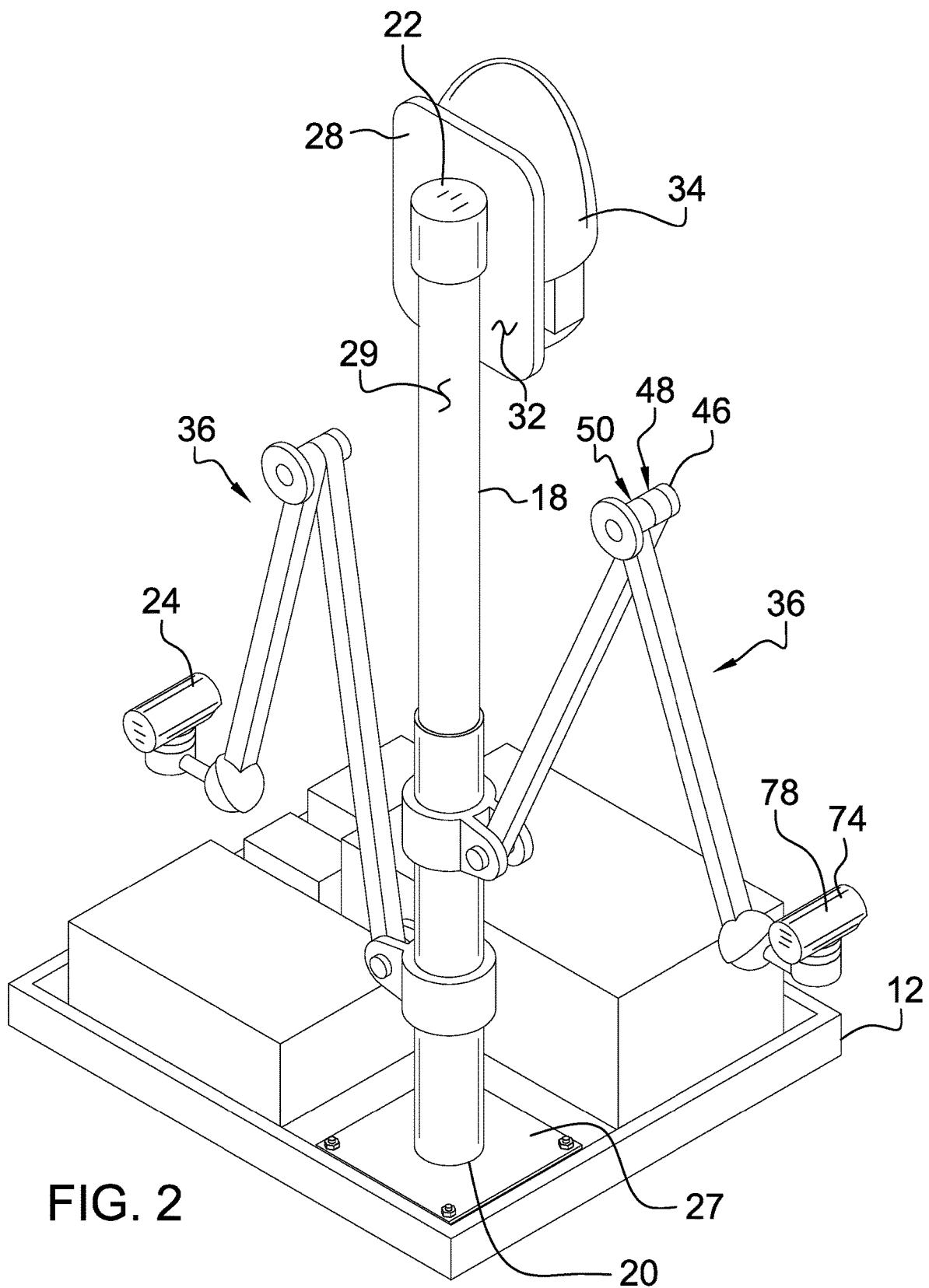
FIG. 2 is a back perspective view of an embodiment of the disclosure.
Figure 3:
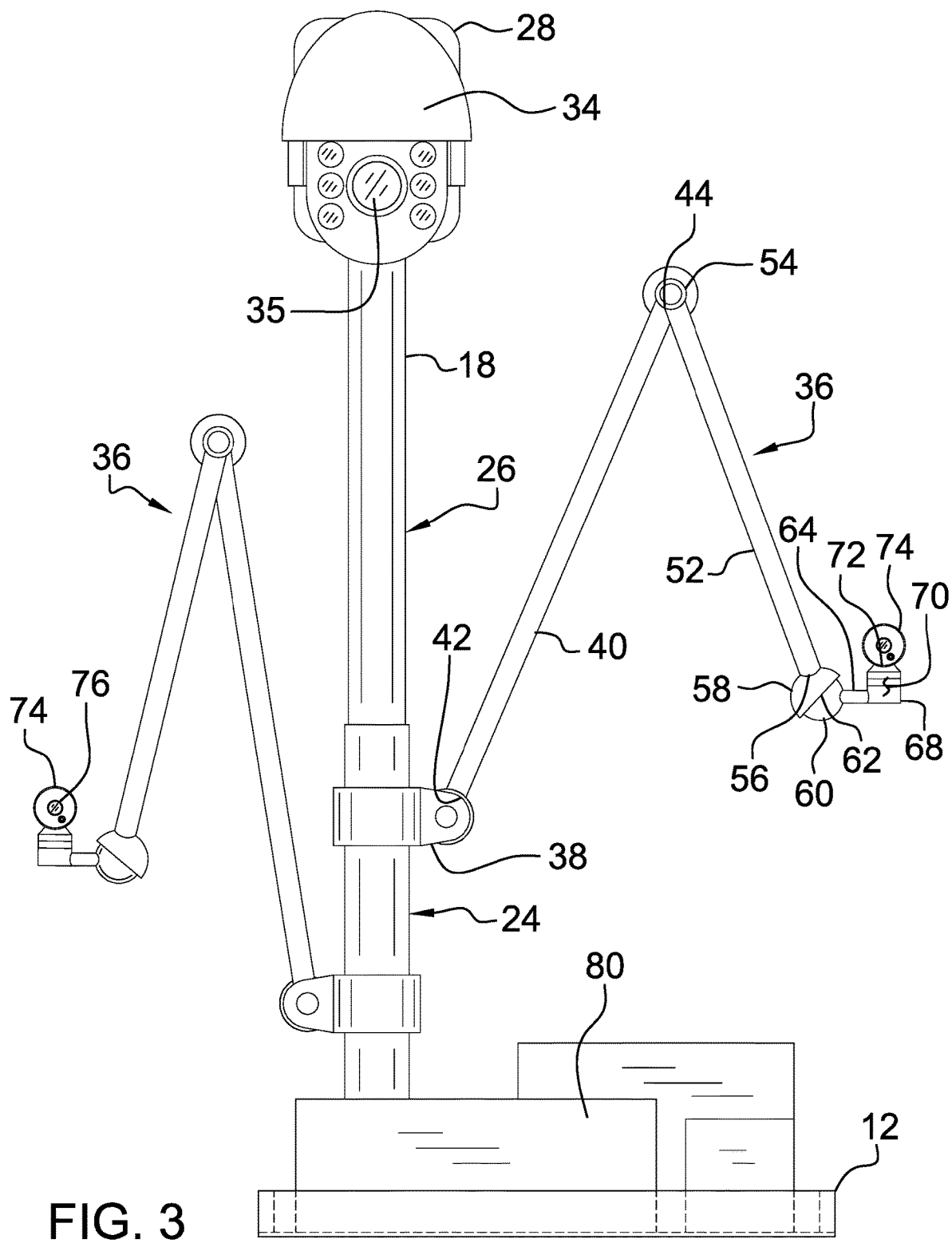
FIG. 3 is a front view of an embodiment of the disclosure.
Figure 4:
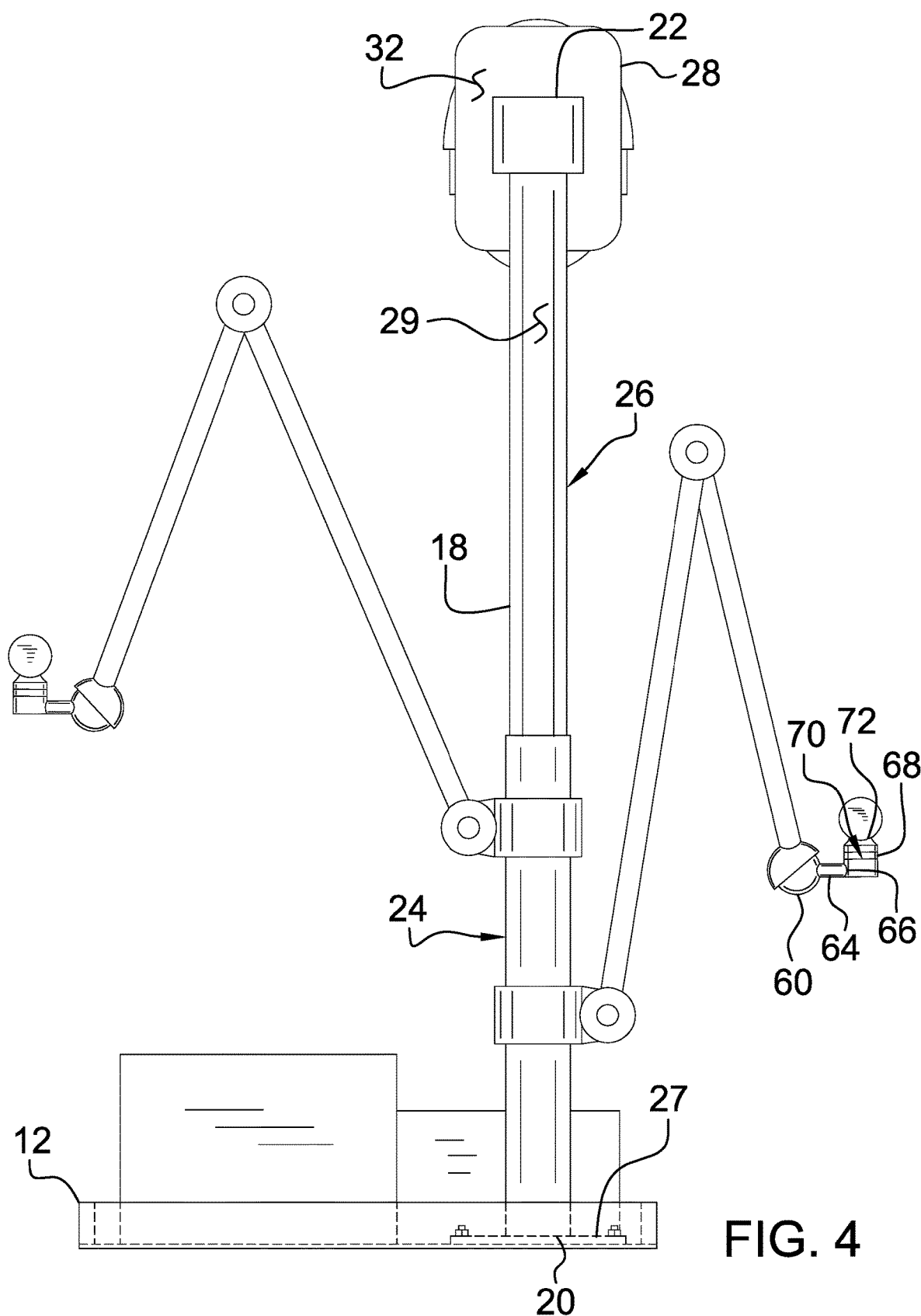
FIG. 4 is a back view of an embodiment of the disclosure.
Figure 5:
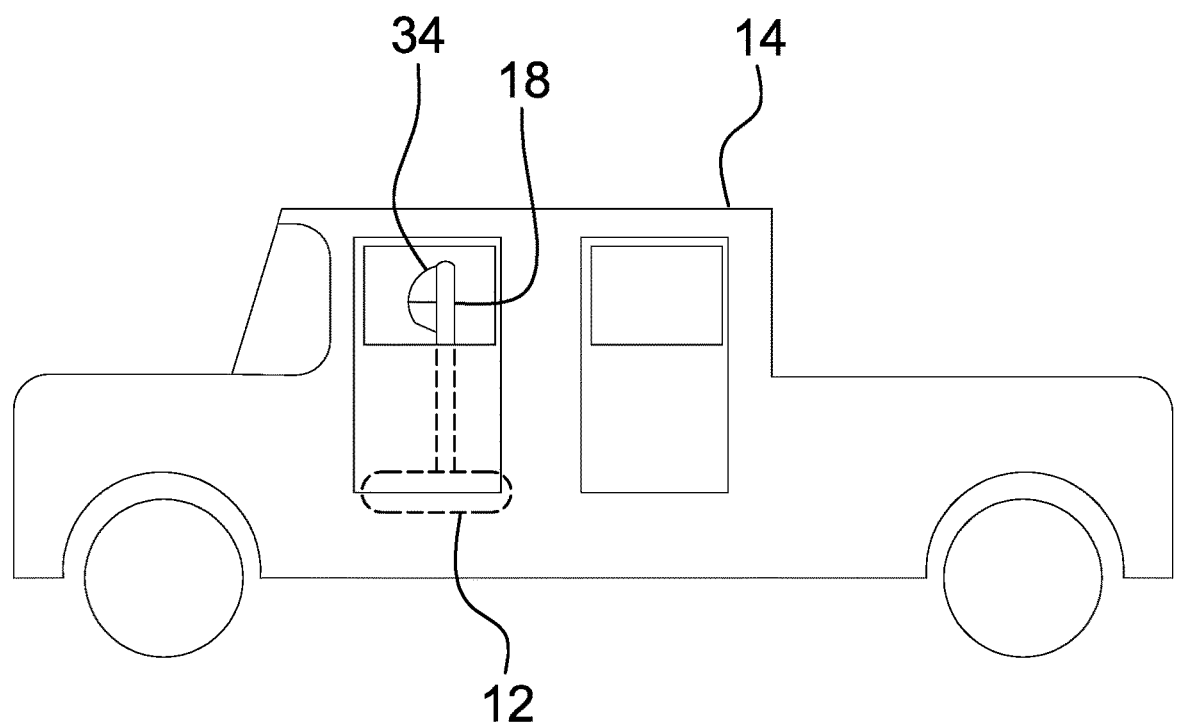
FIG. 5 is a perspective in-use view of an embodiment of the disclosure.
Figure 6:
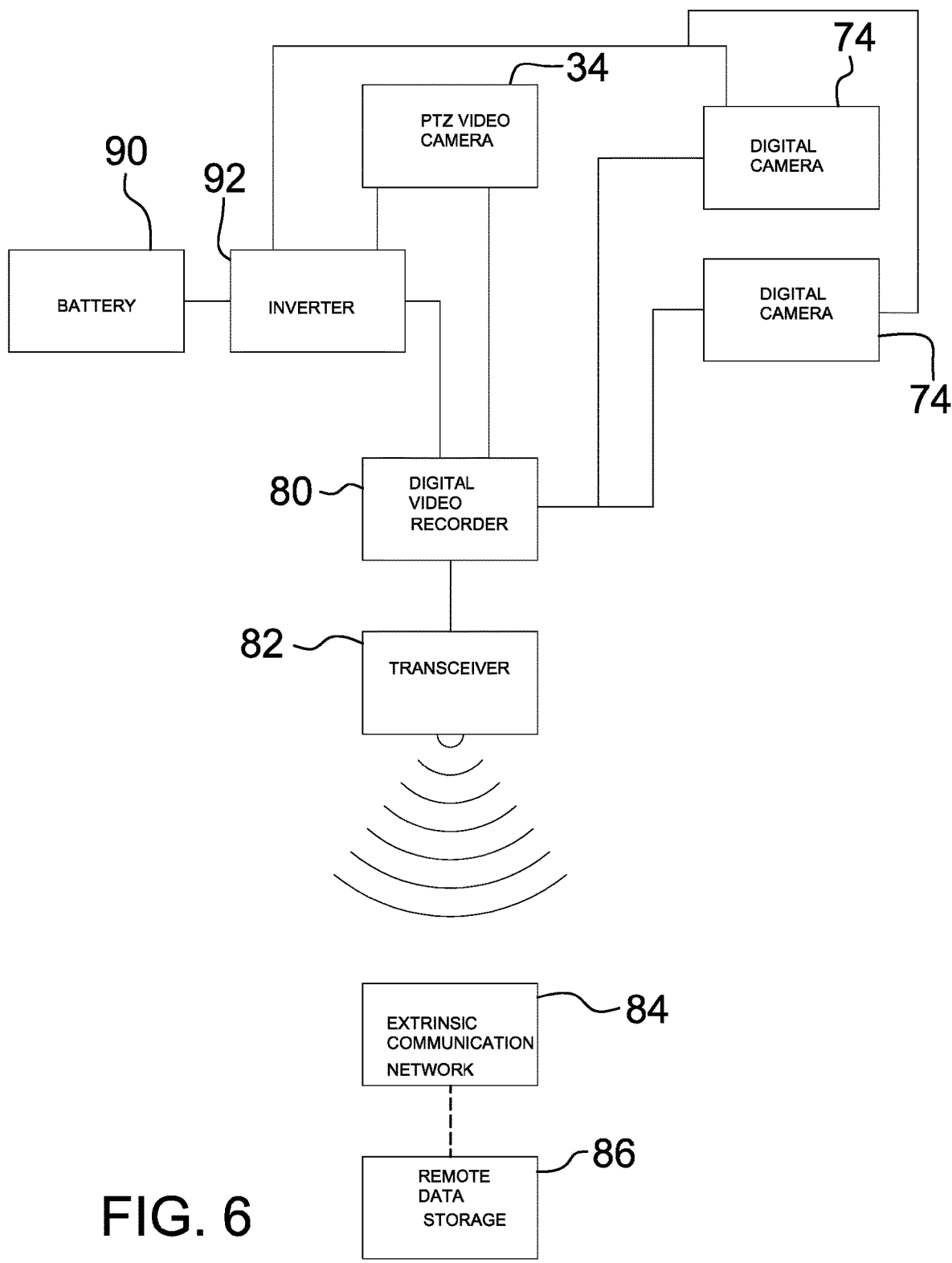
FIG. 6 is a schematic view of an embodiment of the disclosure.

With reference now to the drawings, and in particular to FIGS. 1 through 6 thereof, a new surveillance device embodying the principles and concepts of an embodiment of the disclosure and generally designated by the reference numeral 10 will be described.

As best illustrated in FIGS. 1 through 6, the remote surveillance assembly 10 generally comprises a base 12 that is positionable in a vehicle 14, and the base 12 has a top side 16. The vehicle 14 may be a passenger vehicle, such as a car or the like that is being employed by a private investigator that is conducting surveillance. Additionally, the vehicle 14 may be left unoccupied to inhibit residents from becoming suspicious of a strange person in a parked vehicle. A pole 18 is coupled to and extends upwardly from the base 12. The pole 18 has a first end 20 and a second end 22, and the first end 20 is coupled to the top side 16 of the base 12. The pole 18 comprises a first portion 24 that slidably receives a second portion 26 such that the pole 18 has a telescopically adjustable length. As is most clearly seen in FIG. 2, a mounting plate 27 may be coupled to the first end 22 and the mounting plate 27 may be attached to the top side 16 of the base 12.

A plate 28 is provided that has a front face 30 and a back surface 32, and the back surface 32 is coupled to an outer surface 29 of the pole 18 at a point located adjacent to the second end 22 of the pole 18. A pan tilt zoom (PTZ) video camera 34 is movably disposed on the pole 18 wherein the PTZ video camera 34 to capture surveillance of the environment around the vehicle 14. The PTZ video camera 34 is mounted to the front face 30 of the plate 28 having a lens 35 of the PTZ video camera 34 being directed away from the plate 28. In this way the lens 35 can be directed toward a windshield or other window of the vehicle 14. The PTZ video camera 34 may be a digital PTZ video camera of any conventional design that might include servos, actuators, motors or other similar electronic means of tilting, panning and zooming. Additionally, the PTZ video camera 34 may have night vision capabilities thereby facilitating surveillance footage to be captured at night.

A pair of articulated arms 36 is provided and each of the articulated arms 36 is movably coupled to the pole 18. Each of the articulated arms 36 is positionable in a plurality of orientations with respect to the pole 18. Each of the articulated arms 36 comprises a collar 38 that is rotatably positioned around the first portion 24 of the pole 18. Additionally, each of the articulated arms 36 includes a first rod 40 that has a first end 42 and a second end 44, and the first end 42 of the first rod 40 is pivotally coupled to the collar 38. In this way the first rod 40 can be positioned at a plurality of angles with respect to the first portion 24 of the pole 18.

Each of the articulating arms 36 includes a swivel 46 that comprises a first portion 48 which is rotatably coupled to a second portion 50. Each of the first portion 48 and the second portion 50 is independently rotatable about a common axis, and the second end of the first rod 40 is coupled to the first portion 48. Each of the articulating arms 36 includes a second rod 52 that has a first end 54 and a second end 56. The first end 54 of the second rod 52 is coupled to the second portion 50 of the swivel 46 such that the second rod 52 is positionable at a plurality of angles with respect to the first rod 40.

Each of the articulating arms 36 includes cup 58 that is coupled to the second end 56 of the second rod 52. Moreover, each of the articulating arms 36 includes a ball 60 that is rotatably disposed in the cup 58. The ball 60 has a diameter that is greater than a diameter of an opening 62 in the cup 58 such that the ball 60 is inhibited from being removed from the cup 58. Each of the articulating arms 36 includes a stem 64 that is coupled to and extends away from the ball 60, and the stem 64 has a distal end 66 with respect to the ball 60. Each of the articulating arms 36 includes a mount 68 that has an outer surface 70 and a top end 72, and the outer surface 70 is coupled to the distal end 66 of the stem 64.

A pair of digital cameras 74 is provided and each of the digital cameras 74 is coupled to a respective one of the articulated arms 36 to capture surveillance of the environment around the vehicle 14. Each of the digital cameras 74 is coupled to the top end 72 of the mount 68 of the respective articulated arm 36 having a lens 76 of each of the digital cameras 74 being directed away from the mount 68. In this way the lens 76 of each of the digital cameras 74 can be directed toward the windshield or other window of the vehicle 14. Each of the digital cameras 74 may comprise a static digital video camera of any conventional design. Additionally, each of the digital cameras 74 may include a tubular housing 78 that is attached to the top end 72 of the mount 68.

A digital video recorder 80 is provided and the digital video recorder 80 is coupled to the base 12. The digital video recorder 80 is electrically coupled to the PTZ video camera 34 and each of the digital cameras 74. The digital video recorder 80 records data comprising surveillance footage capture by the PTZ video camera 34 and each of the digital cameras 74. The digital video recorder 80 may comprise an eight channel closed circuit digital video recorder 80 or other similar electronic storage device that is capable of storing at least twenty four hours of video footage.

A transceiver 82 is coupled to the base 12 and the transceiver 82 is in electrical communication with the digital video recorder 80. Additionally, the transceiver 82 is in wireless communication with an extrinsic communication network 84. In this way the transceiver 82 can broadcast the data stored in the digital video recorder 80 to a remote data storage device 86. The transceiver 82 may comprise a radio frequency transceiver or the like and the transceiver 82 may employ a WPAN signal for wirelessly connecting to a wireless internet router.

The extrinsic communication network 84 may comprise the internet, a cellular phone network or any other wireless communication network to facilitate an end user to access the data stored in the remote data storage device 86. Moreover, the end user can download the data stored in the remote data storage device 86 for analysis. Additionally, the end user can stream the video footage in real time from the remote data storage device 86. The end user may be a private investigator, a law enforcement officer or any other person that is authorized to conduct covert surveillance of a designated area.

A power supply 88 is provided and the power supply 88 is coupled to the base 12. The power supply 88 is electrically coupled to the digital video recorder 80, the transceiver 82, the PTZ video camera 34 and each of the digital cameras 74. The power supply 88 comprises a battery 90 that is positioned on the top side 16 of the base 12. An inverter 92 is positioned on the top side 16 of the base 12 and the inverter 92 is electrically coupled to the battery 90 to convert direct current voltage into alternating current voltage.

In use, the base 12 is positioned in a preferred location in the vehicle 14, such as a front seat or the like, and each of the articulated arms 36 is positioned in a preferred orientation to facilitate each of the digital cameras 74 to be pointed in a preferred direction. Additionally, the base 12 is oriented to facilitate the PTZ video camera 34 to be pointed in a preferred direction. The end user can remotely control the PTZ video camera 34 through the transceiver 82 via the extrinsic communication network 84. In this way the end user can conduct real time surveillance with an unoccupied vehicle. Thus, the end user can avoid arousing suspicion that would normally occur with an occupied vehicle that has been parked for an extended period of time.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A remote surveillance assembly for discretely recording surveillance footage in an unoccupied vehicle, said assembly comprising:
   a base being positionable in a vehicle;
   a pole being coupled to and extending upwardly from said base;
   a pan tilt zoom (PTZ) video camera being movably disposed on said pole wherein said PTZ video camera is configured to capture surveillance of the environment around the vehicle;
   a pair of articulated arms, each of said articulated arms being movably coupled to said pole, each of said articulated arms being positionable in a plurality of orientations with respect to said pole;
   a pair of digital cameras, each of said digital cameras being coupled to a respective one of said articulated arms wherein each of said digital cameras is configured to capture surveillance of the environment around the vehicle;
   a digital video recorder being coupled to said base, said digital video recorder being electrically coupled to said PTZ video camera and each of said digital cameras, said digital video recorder recording data comprising surveillance footage capture by said PTZ video camera and each of said digital cameras;
   a transceiver being coupled to said base, said transceiver being in electrical communication with said digital video recorder, said transceiver being in wireless communication with an extrinsic communication network wherein said transceiver is configured to broadcast the data stored in said digital video recorder to a remote data storage device; and
   a power supply being coupled to said base, said power supply being electrically coupled to said digital video recorder, said transceiver, said PTZ video camera and each of said digital cameras, said power supply comprising a battery being positioned on a top side of said base, and
      an inverter being positioned on said top side of said base, said inverter being electrically coupled to said battery wherein said inverter is configured to convert direct current voltage into alternating current voltage.

2. The assembly according to claim 1, wherein said pole having a first end and a second end, said first end being coupled to said top side of said base, said pole comprising a first portion that slidably receives a second portion such that said pole has a telescopically adjustable length.

3. The assembly according to claim 2, wherein said assembly includes a plate having a front face and a back surface, said back surface being coupled to an outer surface of said pole at a point being positioned adjacent to said second end of said pole.

4. The assembly according to claim 3, wherein said PTZ video camera is mounted to said front face of said plate having a lens of said PTZ video camera being directed away from said plate wherein said lens is configured to be directed toward a windshield or other window of the vehicle.

5. The assembly according to claim 2, wherein each of said articulated arms comprises a collar being positioned around said first portion of said pole.

6. The assembly according to claim 5, wherein each of said articulated arms comprises a first rod having a first end and a second end, said first end of said first rod being pivotally coupled to said collar, said first rod being positionable at a plurality of angles with respect to said first portion of said pole.

7. The assembly according to claim 6, wherein each of said articulated arms comprises a swivel comprising a first portion being rotatably coupled to a second portion, each of said first portion and said second portion being independently rotatable about a common axis, said second end of said first rod being coupled to said first portion.

8. The assembly according to claim 7, wherein each of said articulated arms comprises a second rod having a first end and a second end, said first end of said second rod being coupled to said second portion of said swivel, said second rod being positionable at a plurality of angles with respect to said first rod.

9. The assembly according to claim 8, wherein each of said articulated arms comprises a cup being coupled to said second end of said second rod.

10. A remote surveillance assembly for discretely recording surveillance footage in an unoccupied vehicle, said assembly comprising:
    a base being positionable in a vehicle;
    a pole being coupled to and extending upwardly from said base, said pole having a first end and a second end, said first end being coupled to said top side of said base, said pole comprising a first portion that slidably receives a second portion such that said pole has a telescopically adjustable length;
    a pan tilt zoom (PTZ) video camera being movably disposed on said pole wherein said PTZ video camera is configured to capture surveillance of the environment around the vehicle;
    a pair of articulated arms, each of said articulated arms being movably coupled to said pole, each of said articulated arms being positionable in a plurality of orientations with respect to said pole;
    a pair of digital cameras, each of said digital cameras being coupled to a respective one of said articulated arms wherein each of said digital cameras is configured to capture surveillance of the environment around the vehicle;
    a digital video recorder being coupled to said base, said digital video recorder being electrically coupled to said PTZ video camera and each of said digital cameras, said digital video recorder recording data comprising surveillance footage capture by said PTZ video camera and each of said digital cameras;
    a transceiver being coupled to said base, said transceiver being in electrical communication with said digital video recorder, said transceiver being in wireless communication with an extrinsic communication network wherein said transceiver is configured to broadcast the data stored in said digital video recorder to a remote data storage device; and
    wherein each of said articulated arms comprises
       a collar being positioned around said first portion of said pole,
       a first rod having a first end and a second end, said first end of said first rod being pivotally coupled to said collar, said first rod being positionable at a plurality of angles with respect to said first portion of said pole, a swivel comprising a first portion being rotatably coupled to a second portion, each of said first portion and said second portion being independently rotatable about a common axis, said second end of said first rod being coupled to said first portion, a second rod having a first end and a second end, said first end of said second rod being coupled to said second portion of said swivel, said second rod being positionable at a plurality of angles with respect to said first rod, a cup being coupled to said second end of said second rod, and a ball being rotatably disposed in said cup, said ball having a diameter being greater than a diameter of an opening in said cup such that said ball is inhibited from being removed from said cup.

11. The assembly according to claim 10, wherein each of said articulated arms comprises a stem being coupled to and extending away from said ball, said stem having a distal end with respect to said ball.

12. The assembly according to claim 11, wherein each of said articulated arms comprises a mount having an outer surface and a top end, said outer surface being coupled to said distal end of said stem.

13. The assembly according to claim 12, wherein each of said digital cameras is coupled to said top end of said mount of said respective articulated arm having a lens of each of said digital cameras being directed away from said mount wherein said lens of each of said digital cameras is configured to be directed toward the windshield or other window of the vehicle.

14. A remote surveillance assembly for discretely recording surveillance footage in an unoccupied vehicle, said assembly comprising:
- a base being positionable in a vehicle, said base having a top side;
- a pole being coupled to and extending upwardly from said base, said pole having a first end and a second end, said first end being coupled to said top side of said base, said pole comprising a first portion that slidably receives a second portion such that said pole has a telescopically adjustable length;
- a plate having a front face and a back surface, said back surface being coupled to an outer surface of said pole at a point being positioned adjacent to said second end of said pole;
- a pan tilt zoom (PTZ) video camera being movably disposed on said pole wherein said PTZ video camera is configured to capture surveillance of the environment around the vehicle, said PTZ video camera being mounted to said front face of said plate having a lens of said PTZ video camera being directed away from said plate wherein said lens is configured to be directed toward a windshield or other window of the vehicle;
- a pair of articulated arms, each of said articulated arms being movably coupled to said pole, each of said articulated arms being positionable in a plurality of orientations with respect to said pole, each of said articulated arms comprising:
  - a collar being positioned around said first portion of said pole;
  - a first rod having a first end and a second end, said first end of said first rod being pivotally coupled to said collar, said first rod being positionable at a plurality of angles with respect to said first portion of said pole;
  - a swivel comprising a first portion being rotatably coupled to a second portion, each of said first portion and said second portion being independently rotatable about a common axis, said second end of said first rod being coupled to said first portion;
  - a second rod having a first end and a second end, said first end of said second rod being coupled to said second portion of said swivel, said second rod being positionable at a plurality of angles with respect to said first rod;
  - a cup being coupled to said second end of said second rod;
  - a ball being rotatably disposed in said cup, said ball having a diameter being greater than a diameter of an opening in said cup such that said ball is inhibited from being removed from said cup;
  - a stem being coupled to and extending away from said ball, said stem having a distal end with respect to said ball; and
  - a mount having an outer surface and a top end, said outer surface being coupled to said distal end of said stem;
- a pair of digital cameras, each of said digital cameras being coupled to a respective one of said articulated arms wherein each of said digital cameras is configured to capture surveillance of the environment around the vehicle, each of said digital cameras being coupled to said top end of said mount of said respective articulated arm having a lens of each of said digital cameras being directed away from said mount wherein said lens of each of said digital cameras is configured to be directed toward the windshield or other window of the vehicle;
- a digital video recorder being coupled to said base, said digital video recorder being electrically coupled to said PTZ video camera and each of said digital cameras, said digital video recorder recording data comprising surveillance footage capture by said PTZ video camera and each of said digital cameras;
- a transceiver being coupled to said base, said transceiver being in electrical communication with said digital video recorder, said transceiver being in wireless communication with an extrinsic communication network wherein said transceiver is configured to broadcast the data stored in said digital video recorder to a remote data storage device; and
- a power supply being coupled to said base, said power supply being electrically coupled to said digital video recorder, said transceiver, said PTZ video camera and each of said digital cameras, said power supply comprising:
- a battery being positioned on said top side of said base; and
- an inverter being positioned on said top side of said base, said inverter being electrically coupled to said battery wherein said inverter is configured to convert direct current voltage into alternating current voltage.

* * * * *